United States Patent [19]

Huser et al.

[11] Patent Number: 5,037,998

[45] Date of Patent: Aug. 6, 1991

[54] HYDROGENOLYSIS PROCESS

[75] Inventors: Marc Huser; John Osborn, both of Strasbourg, France

[73] Assignee: Rhone-Poulenc Chimie, Courbevoie Cedex, France

[21] Appl. No.: 383,075

[22] Filed: Jul. 20, 1989

[30] Foreign Application Priority Data

Jul. 20, 1988 [FR] France ............... 88 09790

[51] Int. Cl.$^5$ .......... C07C 1/20; B01J 31/00
[52] U.S. Cl. ................. 585/469; 502/162; 208/262.1
[58] Field of Search ............ 208/262.1; 502/162; 585/469

[56] References Cited

U.S. PATENT DOCUMENTS 3,595,931  7/1971  Hay et al. .................. 585/469
4,400,566  8/1983  Colon ........................ 585/469
4,582,817  4/1986  Hanes ........................ 502/162

OTHER PUBLICATIONS

Henderson, Jr. et al., "The Basicity of Phosphines", Journal of the American Chemical Society, 82, pp. 5791–5794 (1960).

Tolman, "Phosphorus Ligand Exchange Equilibria on Zerovalent Nickel a Dominant Role for Steric Effects", Journal of the American Chemical Society, 92, pp. 2956–2965 (1970).

Primary Examiner—Curtis R. Davis
Assistant Examiner—Nhat Phan
Attorney, Agent, or Firm—Finnegan, Henderson, Farabow, Garrett, and Dunner

[57] ABSTRACT

A process of hydrogenolysis utilizing a new catalyst consisting of a palladium phosphine complex, the phosphien having a pKa greater than or equal to 6, a chlorinated aromatic compound and hydrogen.

30 Claims, No Drawings

HYDROGENOLYSIS PROCESS

FIELD OF THE INVENTION

The present invention relates to a hydrogenolysis process. It relates more particularly to the hydrogenolysis of chlorinated aromatic compounds in the presence of a palladium-based catalyst. More particularly, the present invention provides a process for the hydrogenolysis of a halogenated aromatic compound which comprises contacting a chloroaromatic compound, a catalyst based on palladium, and a phosphine which has a pKa greater than or equal to 6, with hydrogen.

BACKGROUND OF THE INVENTION

It is advantageous to perform the hydrogenolysis of chlorinated aromatic compounds when, for example, it is necessary to retain one or more substituents which have been introduced into a precise position of the aromatic nucleus only by virtue of the chlorine atom.

At present, the present inventors do not know of any documents describing the hydrogenolysis of chlorinated compounds by means of catalysts in a homogeneous phase.

DESCRIPTION OF THE INVENTION

The present invention has made it possible to attain this objective, that is to say it is now possible to hydrogenolyze a chlorinated aromatic compound in a homogeneous liquid phase in the presence of a palladium-based catalyst.

The palladium-based catalyst is selected particularly from complexes of palladium and of a phosphine. This phosphine must have a pKa greater than 6, such as defined by Wm. A. Henderson, Jr. and C. A. Streuli in the Journal of the American Chemical Society, 82: 5791 (1960).

Among the phosphines which have a pKa greater than 6 there may be mentioned, no limitation being implied:
tricyclohexylphosphine
tribenzylphosphine
triisopropylphosphine
triisobutylphosphine
phenyldicyclohexylphosphine
triethylphosphine
tributylphosphine
tripropylphosphine
dicyclohexylphenylphosphine Among all these phosphines, it is preferred to employ those which have both a pKa greater than 6 and a cone angle of from 160 to 180° as defined by C. A. Tolman in the Journal of the American Chemical Society, 92: 2956 (1970).

The following phosphines in particular are included within this range:
tricyclohexylphosphine
dicyclohexylphenylphosphine
triisopropylphosphine
tribenzylphosphine It is especially preferred to employ tricyclohexylphosphine. One preferred complex of the present invention corresponds to the following formula (I)

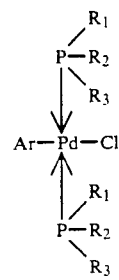

in which
each of $R_1$, $R_2$ and $R_3$ is an identical or different group selected from cyclohexyl, benzyl and isopropyl radicals, it being possible for one of the groups $R_1$, $R_2$ or $R_3$ to be replaced by a phenyl group when the other two are cyclohexyl groups and
Ar is an optionally substituted mono-, polycyclic or heterocyclic aromatic radical.

The complex of formula (I) described above is employed especially to catalyze the hydrogenolysis reaction. In one embodiment, a palladium complex of the above formula (I) is introduced into a solvent with a chloroaromatic compound and hydrogen, optionally in the presence of an excess of phosphine. This hydrogenolysis reactions proceeds according to the following reaction mechanism:

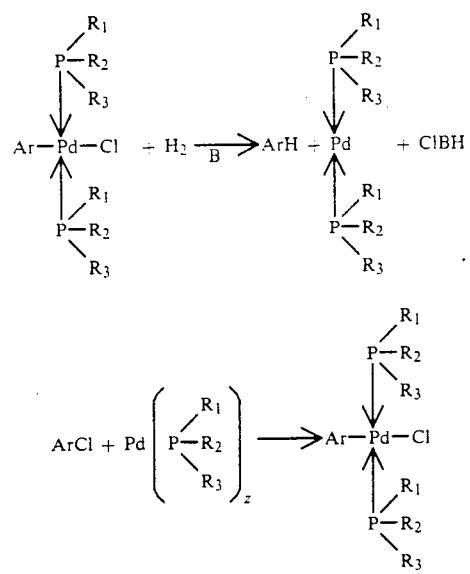

which can be summarized in a simplified way by the following equation:

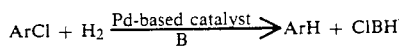

In the above equations, the terms $R_1$, $R_2$ and $R_3$ mean either a cyclohexyl group, a phenyl group, a benzyl group, or an isopropyl group. The phosphorus can be coordinated with 3 equivalent ligand groups, as in tricyclohexylphosphine, or by different groups, as in dicyclohexylphenylphosphine. The term "B" means a base.

Ar may be an unsubstituted or a substituted mono-, polycyclic or heterocyclic aromatic radical.

The chlorinated aromatic compound (ArCl) may be mono-, polycyclic or heterocyclic. It may be optionally substituted by an alkoxy, alkyl, alkylcarbonyl, cycloalkyl, cycloalkoxy, halo, haloalkyl, haloalkoxy, halocycloalkyl, halocycloalkoxy, aryl, aryloxy, haloaryl, haloaryloxy, alkylaryl, aralkyl, alkylcarbonyloxy, cycloalkylcarbonyloxy, arylcarbonyloxy or aryloxycarbonyl group.

In one embodiment, Ar is a monocyclic aromatic radical, or is a monocyclic aromatic radical substituted by an alkyl, alkoxy, alkylcarbonyl, cycloalkyl, cycloalkoxy, alkylcarbonyloxy, cycloalkylcarbonyloxy, aryl, aralkyl, alkylaryl, aryloxy, arylcarbonyloxy, aryloxycarbonyl, halo, haloalkyl, haloalkoxy, halocycloalkyl, halocycloalkoxy, haloaryl or haloaryloxy group, the alkyl or alkoxy moieties containing from 1 to 12 carbon atoms.

The alkyl chains of the various alkyl or alkoxy groups preferably contain 1 to 6 carbon atoms; the aryl groups preferably contain 6 to 18 carbon atoms.

It is preferred to employ the monocyclic aromatic compounds which are unsubstituted or substituted by an alkoxy group containing 1 to 6 carbon atoms, an alkyl group containing 1 to 6 carbon atoms, or a chloro, fluoro, or alkylcarbonyl group whose alkyl chain contains 1 to 6 carbon atoms.

Among the chlorinated aromatic compounds which can be employed in the process of the invention there may be mentioned, by way of illustration:
chlorobenzene
dichlorobenzene
chlorofluorobenzene
chlorotoluenes
chloroanisoles
chloronaphthalenes
methyl, ethyl or propyl chlorobenzoates
methyl chlorophenyl ketone
chlorobiphenyls
chloroindole
chlorothiophene
ethyl ester of chlorobenzoic acid Among the preferred compounds, ArCl can be chloro-benzene, chloroanisole or the ethyl ester of chlorobenzoic acid.

A base (B) is needed to neutralize the hydrochloric acid formed during the hydrogenolysis reaction. This base may consist of the phosphine itself or of a different base. If this base is different, it preferably has a pKa higher than that of the phosphine, so that the latter should not act unnecessarily as a neutralizing base.

The base is preferably soluble in the reaction mixture. In one embodiment, the base is selected from a tertiary amine and an inorganic base and is added in a molar quantity greater than the aromatic compound. It is preferred to employ tertiary amines such as trialkylamines and, for example, triethylamine, triisopropylamine or tri-n-butylamine. Inorganic bases, such as sodium carbonate, can also be employed but offer no particular advantage.

The solvent employed for making use of the invention is selected from optionally halogenated solvents such as: aromatic hydrocarbons such as:
toluene
xylenes
  ethers such as:
dioxane
  alcohols, such as:
ethanol
  isopropanol
  ketones, such as:
methyl isobutyl ketone
  nitriles such as:
benzonitrile
  amides, such as:
dimethylformamide
  and aliphatic hydrocarbons.

Reactants such as the chloroaromatic compound or the base can serve as a reaction medium.

The complex of formula I may be employed as such as a catalyst.

The complex of formula I may also be formed in situ by at least three methods of implementation.

According to a first method of implementing the process of the invention, a compound of the following formula (II):

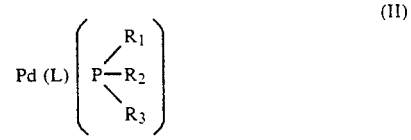

in which
the moiety L is a group which is labile in the presence of ArCl, and
the groups $R_1$, $R_2$ and $R_3$ have the same meaning as in formula (I), is brought into contact with an aromatic halo compound of the formula ArCl and hydrogen in a solvent.

In one embodiment, a palladium complex of the above formula (II) is introduced into a solvent with a chloroaromatic compound and hydrogen, optionally in the presence of an excess of phosphine.

According to a second method of implementing the process of the invention, a complex of palladium in the zero oxidation state, such as:

Pd (L)$_3$ and at least two equivalents of phosphine corresponding to the formula

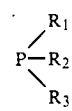

are brought into contact with a chloroaromatic compound of formula ArCl and hydrogen.

In one embodiment of this second method, a palladium complex of formula Pd (L)$_3$, in which L is dibenzylideneacetone or an alkylene group, a chloroaromatic compound and hydrogen are introduced into a solvent in the presence of a phosphine of the formula:

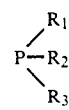

in which
each of $R_1$, $R_2$ and $R_3$ is identical or different and is selected from cyclohexyl, benzyl and isopropyl radicals with the proviso that one of $R_1$, $R_2$ or $R_3$ can be replaced by a phenyl group when the other two are cyclohexyl groups.

According to a third method of implementing the process of the invention, a salt of palladium in the oxidation state II, selected, for example, from palladium dichloride, dibromide or diiodide, palladium diacetate, palladium dinitrate, palladium sulfate and palladium oxide is brought into contact with the chloroaromatic compound and at least two equivalents of phosphine of the formula

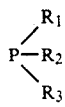

and in the presence of hydrogen.

In one embodiment of this third method, a complex of palladium in the oxidation state II, a chloroaromatic compound and hydrogen are introduced into a solvent in the presence of a phosphine of formula

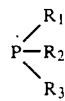

in which each of $R_1$, $R_2$ and $R_3$ is identical or different and is selected from cyclohexyl, benzyl and isopropyl radicals with the proviso that one of $R_1$, $R_2$ or $R_3$ can be replaced by a phenyl group when the other two are cyclohexyl groups.

Within the scope of the present invention, a labile group (L) means any group which can be easily exchangeable in the presence of ArCl. Among these groups there may be mentioned, no limitation being implied:
dibenzylideneacetone (DBA)
alkylene, and preferably ethylene, groups.

When starting with a palladium complex not containing phosphine (second or third methods of implementation), it is preferred to employ at least 2 moles of phosphine per gram-atom of palladium, more preferably from 2 to 10,000 moles, and even more preferably from 2 to 5 moles.

It is preferred that the quantity of palladium, expressed in milligram-atoms of noble metal or in millimoles of metal compound per liter, is from $10^{-5}$ to 100. It is preferred to employ a quantity of solvent such as to make the palladium salt or complex concentration in the medium from $10^{-5}$ to 100 moles per liter.

In one embodiment, the reaction takes place in an excess of reactant or in the presence of a solvent selected from unsubstituted or halogenated aromatic or aliphatic hydrocarbon compounds, ethers, alcohols, ketones, amides and nitriles.

The minimum base concentration must correspond to the stoichiometry of the reaction. It may be employed in a quantity which is markedly greater, and can even be employed as a solvent. It is desirable that the base should not be exhausted when the reaction is finished.

The concentration of the chlorinated aromatic compound may vary within wide limits, since it can be employed as a solvent. In this case, it is easily recycled.

The reaction temperature is preferably from 50° to 250° C. and more preferably from 100° to 200° C.

The partial pressure of hydrogen is preferably from 1 to 300 bars and more preferably from 10 to 100 bars.

The present invention will be described more completely with the aid of the following examples, which should not be considered as limiting the invention.

In the following examples, the following abbreviations have the noted meanings:

$PCY_3$ = tricyclohexylphosphine.

DC = degree of conversion (quantity of halogenated aromatic compound converted)/(quantity of halogenated aromatic compound introduced) $\times$ 100.

CY = yield based on converted product (quantity of desired product formed (mol))/(quantity of product converted (mol)) $\times$ 100.

EXAMPLES 1 TO 4

INFLUENCE OF THE NATURE OF THE PHOSPHINE

The following were introduced into a reactor made of Hastelloy HB2 ®:
1 mg-at. of palladium diacetate
5 mmol of $PL_3$, L being varied
50 mmol of $RC_6H_4Cl$
110 mmol of $NEt_3$
toluene q.s. 30 ml.

The reactor was kept under a hydrogen pressure of 15 bars at a temperature of 180° C. for 4 hours. The results are shown in the following Table I.

TABLE I

| Example | R | Phosphine $PL_3$ | DC % | CY(p-RC$_6$H$_5$) % |
|---|---|---|---|---|
| 1 | H | PCy$_3$ | 29 | 100 |
| 2 | H | PBz$_3$ | 41 | 85 |
| 3 | COOEt | PBz$_3$ | 48 | 88 |
| 4 | H | PEt$_3$ | 10 | 100 |

A comparative test was carried out, the phosphine $PL_3$ being replaced by a phosphine which had a pKa of less than 6, i.e., triphenylphosphine. The mixture became heterogeneous and the test had to be stopped.

EXAMPLES 5 AND 6

INFLUENCE OF THE NATURE OF A SUBSTITUENT ON p-RC$_6$H$_4$Cl

The following were introduced into the same reactor as in Examples 1-4:
1 mg-at. of Pd(OAc)$_2$
5 mmol of PCy$_3$
50 mmol of p-RC$_6$H$_4$Cl
110 mmol of NEt$_3$
toluene q.s. 30 ml.

The reactor was kept under a hydrogen pressure of 15 bars at a temperature of 180° C. for 4 hours. The results are shown in the following Table II.

TABLE II

| Example | R | DC % | CY(p-RC$_6$H$_5$) % |
|---|---|---|---|
| 5 | OMe | 22 | 82 |
| 1 | H | 29 | 100 |
| 6 | COOEt | 86 | 100 |

EXAMPLE 7

INFLUENCE OF THE CONCENTRATION OF THE BASE

Example 1 was repeated using 5 mmol of $PCy_3$ and 179 mmol of $NEt_3$. The results are shown in the following Table III

TABLE III

| Example | [NEt$_3$] | DC % | CY(C$_6$H$_6$) % |
|---|---|---|---|
| 1 | 100 | 29 | 100 |
| 7 | 179 | 52 | 98 |

A comparative test was performed with an amine (pyridine) which had a pKa lower than that of phosphine; the degree of conversion of the chlorobenzene was nil.

What is claimed is:

1. A process for the hydrogenolysis of a halogenated aromatic compound which comprises contacting a chloroaromatic compound, a catalyst containing palladium, and a phosphine which has a pKa greater than or equal to 6, with hydrogen.

2. The process as claimed in claim 1, wherein the chloroaromatic compound corresponds to the formula ArCl in which Ar is an unsubstituted or a substituted mono-, polycyclic or heterocyclic aromatic radical.

3. The process as claimed in claim 2, wherein Ar is a monocyclic aromatic radical, or is a monocyclic aromatic radical substituted by an alkyl, alkoxy, alkylcarbonyl, cycloalkyl, cycloalkoxy, alkylcarbonyloxy, cycloalkylcarbonyloxy, aryl, aralkyl, alkylaryl, aryloxy, arylcarbonyloxy, aryloxycarbonyl, halo, haloalkyl, haloalkoxy, halocycloalkyl, halocycloalkoxy, haloaryl or haloaryloxy group, the alkyl or alkoxy moieties containing from 1 to 12 carbon atoms.

4. The process as claimed in claim 3, wherein the compound ArCl is chlorobenzene, chloroanisole or the ethyl ester of chlorobenzoic acid.

5. The process as claimed in claim 1, wherein the phosphine has a cone angle of from 160° to 180°.

6. The process as claimed in claim 5, wherein the phosphine is selected from tricyclohexylphosphine, dicyclohexylmonophenylphosphine, tribenzylphosphine, triisopropylphosphine, triethylphosphine and tributylphosphine.

7. The process as claimed in claim 6, wherein the phosphine is tricyclohexylphosphine.

8. The process as claimed in claim 1, wherein the phosphine is selected from tricyclohexylphosphine, dicyclohexylmonophenylphosphine, tribenzylphosphine, triisopropylphosphine, triethylphosphine and tributylphosphine.

9. The process as claimed in claim 8, wherein the phosphine is tricyclohexylphosphine.

10. The process as claimed in claim 1, wherein a base is selected from a tertiary amine and an inorganic base is added in a molar quantity greater than the aromatic compound.

11. The process as claimed in claim 1, wherein the reaction takes place in an excess of reactant or in the presence of a solvent selected from unsubstituted or halogenated aromatic or aliphatic hydrocarbon compounds, ethers, alcohols, ketones, amides and nitriles.

12. The process as claimed in claim 1, wherein the quantity of palladium, expressed in milligram-atoms of noble metal or in millimoles or metal compound per liter, is from $10^{-5}$ to 100.

13. The process as claimed in claim 12, wherein the quantity of phosphine is such that the number of moles of phosphine to the number of the gram-atoms of palladium is from 2:1 to 10,000:1.

14. The process as claimed in claim 13, wherein the quantity of phosphine is such that the number of moles of phosphine to the number of the gram-atoms of palladium is from 2:1 to 5:1.

15. The process as claimed in claim 1, wherein the quantity of phosphine is such that the number of moles of phosphine to the number of the gram-atoms of palladium is from 2:1 to 10,000:1.

16. The process as claimed in claim 15, wherein the quantity of phosphine is such that the number of moles of phosphine to the number of the gram-atoms of palladium is from 2:1 to 5:1.

17. The process as claimed in claim 1, wherein the reaction pressure is from 1 to 300 bars.

18. The process as claimed in claim 17, wherein the reaction pressure is from 10 to 100 bars.

19. The process as claimed in claim 1, wherein the reaction temperature is from 50° to 250° C.

20. The process as claimed in claim 19, wherein the reaction temperature is from 100° to 200° C.

21. A process of hydrogenolysis which comprises introducing into a solvent a chloroaromatic compound, hydrogen, phosphine, and a palladium complex of following formula (I)

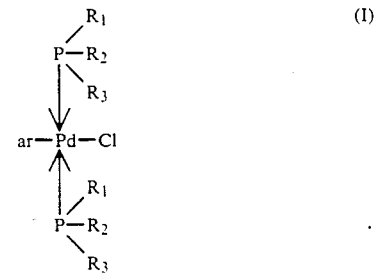

in which
each of $R_1$, $R_2$ and $R_3$ is identical or different and is selected from cyclohexyl, benzyl and isopropyl radicals with the proviso that one of $R_1$, $R_2$ or $R_3$ can be replaced by a phenyl group when the other two are cyclohexyl groups and Ar is a mono-, polycyclic or heterocyclic aromatic radical.

22. A process of hydrogenolysis which comprises introducing into a solvent a chloroaromatic compound, hydrogen, phosphine, and a palladium complex of the following formula (II)

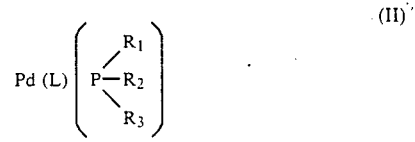

in which
each of $R_1$, $R_2$ and $R_3$ is identical or different and is selected from cyclohexyl, benzyl and isopropyl radicals with the proviso that one of $R_1$, $R_2$ or $R_3$ can be replaced by a phenyl group when the other two are cyclohexyl groups and L is dibenzylideneacetone or an alkylene group.

23. A process of hydrogenolysis which comprises introducing a palladium complex of formula Pd(L)$_3$ in which L is dibenzylideneacetone or an alkylene group, a chloroaromatic compound and hydrogen into a solvent in the presence of a phosphine of the formula

in which
each of $R_1$, $R_2$ and $R_3$ is identical or different and is selected from cyclohexyl, benzyl and isopropyl radicals with the proviso that one of $R_1$, $R_2$ or $R_3$ can be replaced by a phenyl group when the other two are cyclohexyl groups.

24. A process for hydrogenolysis which comprises introducing a complex of palladium in the oxidation state (II), a chloroaromatic compound and hydrogen into a solvent in the presence of a phosphine of the formula

in which
each of $R_1$, $R_2$ and $R_3$ is identical or different and is selected from cyclohexyl, benzyl and isopropyl radicals with the proviso that one of $R_1$, $R_2$ or $R_3$ can be replaced by a phenyl group when the other two are cyclohexyl groups.

25. The process as claimed in claim 24, wherein the complex of palladium in the oxidation state II is selected form palladium dichloride, dibromide or diiodide, palladium diacetate, palladium dinitrate, palladium sulfate and palladium oxide.

26. The process as claimed in claim 1, wherein the palladium containing catalyst and the phosphine are a catalyst complex comprising palladium and a phosphine which has a pKa greater than or equal to 6.

27. The process as claimed in claim 21, wherein the phosphine is in excess.

28. The process as claimed in claim 21, wherein the phosphine is not in excess.

29. The process as claimed in claim 22, wherein the phosphine is in excess.

30. The process as claimed in claim 22, wherein the phosphine is not in excess.

UNITED STATES PATENT AND TRADEMARK OFFICE
CERTIFICATE OF CORRECTION

PATENT NO. : 5,037,998

DATED : August 06, 1991

INVENTOR(S) : Marc Huser et al.

It is certified that error appears in the above-identified patent and that said Letters Patent is hereby corrected as shown below:

Claim 25, column 10, line 15, change "form" to --from--.

Column 5, line 1, change "form" to --from--.

Signed and Sealed this

Twenty-third Day of March, 1993

Attest:

STEPHEN G. KUNIN

*Attesting Officer*     Acting Commissioner of Patents and Trademarks